US008010301B2

(12) United States Patent
Hlavaty

(10) Patent No.: US 8,010,301 B2
(45) Date of Patent: *Aug. 30, 2011

(54) METHOD AND SYSTEM FOR MONITORING CHANGES IN A SAMPLE FOR A PROCESS OR AN ENVIRONMENT

(75) Inventor: Charles W. Hlavaty, O Fallon, MO (US)

(73) Assignee: The Boeing Company, Chicago, IL (US)

( * ) Notice: Subject to any disclaimer, the term of this patent is extended or adjusted under 35 U.S.C. 154(b) by 539 days.

This patent is subject to a terminal disclaimer.

(21) Appl. No.: 12/058,142

(22) Filed: Mar. 28, 2008

(65) Prior Publication Data

US 2009/0248322 A1    Oct. 1, 2009

(51) Int. Cl.
*G01N 31/00* (2006.01)
*G01J 5/02* (2006.01)

(52) U.S. Cl. ...................... 702/28; 250/341.8

(58) Field of Classification Search .............. 702/28, 702/19, 22–23, 26–27, 29–32, 40, 49–50, 702/75–77, 79, 81, 84, 127–128, 134, 137, 702/182–183, 188–189; 250/330, 332–333, 250/341.1, 341.8, 390.04, 390.07, 491.1, 250/492.1, 580

See application file for complete search history.

(56) References Cited

U.S. PATENT DOCUMENTS

| | | | |
|---|---|---|---|
| 5,939,721 A * | 8/1999 | Jacobsen et al. | 250/330 |
| 6,747,736 B2 * | 6/2004 | Takahashi | 356/319 |
| 6,815,683 B2 * | 11/2004 | Federici et al. | 250/341.1 |
| 7,663,107 B2 * | 2/2010 | Taday | 250/339.11 |
| 7,835,873 B2 * | 11/2010 | Hlavaty | 702/31 |
| 2003/0100824 A1 | 5/2003 | Warren et al. | |
| 2004/0095147 A1 * | 5/2004 | Cole | 324/629 |
| 2004/0227088 A1 * | 11/2004 | Trotz et al. | 250/341.1 |
| 2005/0056785 A1 * | 3/2005 | Chou et al. | 250/338.1 |
| 2006/0231762 A1 * | 10/2006 | Ohtake et al. | 250/341.8 |
| 2007/0010702 A1 | 1/2007 | Wang et al. | |
| 2007/0114419 A1 * | 5/2007 | Bastiaans et al. | 250/341.8 |
| 2008/0106733 A1 | 5/2008 | Swift et al. | |
| 2008/0203306 A1 * | 8/2008 | Zhang et al. | 250/341.1 |
| 2008/0258071 A1 * | 10/2008 | Arnold et al. | 250/373 |
| 2009/0065697 A1 * | 3/2009 | Siegel et al. | 250/339.11 |
| 2009/0206263 A1 * | 8/2009 | Rahman | 250/341.1 |

OTHER PUBLICATIONS

Campbell et al., Non-Invasive Detection of Weapons of Mass Destruction Using THz Radiation, 2003, SPIE, vol. 5070, pp. 38-43.*

(Continued)

*Primary Examiner* — Mohamed Charioui
*Assistant Examiner* — Toan M Le
(74) *Attorney, Agent, or Firm* — Moore & Van Allen PLLC; W. Kevin Ransom

(57) ABSTRACT

Systems and methods for monitoring a sample or a sample flow associated with a process or an environment. The systems and methods transmit terahertz signals at the sample, receive a resulting spectral response, perform a spectral analysis, and display a result or choose a course of action. The analysis compares the sample's absorption or reflection spectral response to known spectrums to determine composition; or to determine if the sample flow has deviated from "normal". In one embodiment, the systems and methods use reflection terahertz on a contained sample; in another it uses transmission terahertz to look at a sample flow outside the vehicle. In this embodiment the analysis is used to determine sample composition. In other embodiments, the analysis is used to discern or warn of changes, or to choose a course of action.

38 Claims, 3 Drawing Sheets

OTHER PUBLICATIONS

Woolard et al., Terahertz-Frequency Remote Sensing of Biological Warfare Agents, 2003 IEEE, pp. 763-766.*

Woolard et al., Terahertz Frequency Sensing and Imaging: A Time of Reckoning Future Applications?, Oct. 2005, Proceedings of the IEEE, vol. 93, No. 10, pp. 1722-1743.*

Katharyn S. Kalasinsky, Ted Hadfield, April A. Shea, Victor F. Kalasinsky, Matthew P. Nelson, Jason Neiss, Amy J. Drauch, G. Steven Vanni, and Patrick J. Treado, Raman Chemical Imaging Spectroscopy Reagentless Detection and Identification of Pathogens: Signature Development and Evaluation, Analytical Chemistry, Apr. 1, 2007, 2658-2673, vol. 79, No. 7, US.

* cited by examiner

METHOD AND SYSTEM FOR MONITORING CHANGES IN A SAMPLE FOR A PROCESS OR AN ENVIRONMENT

BACKGROUND OF THE INVENTION

The present invention relates generally to detection of the composition of a sample, and more particularly to methods and systems for detecting chemical and/or biological agents in a sample or samples or detecting a chemical/biological change in composition of a sample flow.

Various testing systems have been developed to detect harmful biological agents in samples. Many of these conventional systems use chemical reactions applied to a contained sample over a given time period. By monitoring these chemical reactions, an analysis of the sample is made and identifications of biological agents, if present, are determined. While these conventional systems provide accurate results, there are many drawbacks associated with their use.

In particular, there may be significant delay between the time the sample is received and the results are determined. Chemical reactions take time to occur and process, which introduces delay. Further, systems that use chemical reactions as part of sample testing may require special environmental considerations (e.g., space, temperature control, specialized equipment, etc.) that may make use of such systems impractical for some applications. Chemical reaction analysis solutions are generally complex, too large, and too heavy. They often require sample preparation and minutes to hours to obtain results. Further, they may be limited to a discrete number of analyses before the equipment must be reset or the chemicals used in the reactions replaced.

BRIEF SUMMARY OF THE INVENTION

The present invention provides systems and methods for detecting changes in a sample and/or the presence of one or more of a chemical and/or a biological agent present in a sample. The systems and methods use spectral analysis, rather than chemical reactions, to assess the content of the sample. The systems and methods thus eliminate the complex mechanisms needed for sample collection, concentration, isolation, and preparation to obtain a chemical reaction. Where a chemical-based solution is limited to a discrete number of analyses between replenishment of supplies, the systems and methods of the present invention may provide real time, continuous, near real time, or substantially continuous analysis of a sample or sample flow.

These advantages mean that the systems and methods of the present invention may be used for real-time evaluation. For example, when used in a vehicle, the systems and methods may be used to map a hazardous plume, or help guide a vehicle to either seek the area of highest concentration, or turn to avoid the hazardous plume. It can also be used as an alarm to declare that vehicle decontamination must be accomplished due to exposure to hazardous material and identify the contents of exposure. Its real-time capability immediately informs vehicle occupants that they should take appropriate actions due to exposure, enables immediate broadcast of warnings to others nearby, and its material identification can help guide choices in immediate medical treatment. By digitally recording its measurements of spectral signatures, it may provide a permanent record that can be used to substantiate exposures or enable further analysis post mission.

The systems and methods of the present invention may also be used to control various processes. For example, the system and methods may be used to monitor a sample associated with a process. The systems and methods of one embodiment may be used to provide alerts when a content of the sample reaches a threshold level. The systems and methods of some embodiments may provide feedback to the process for altering the process based on the analysis of the sample. In some embodiments, the systems and methods may further determine a cause for changes in the process that caused the level of a content of the sample and may provide feedback to the process to regulate its control mechanisms.

In one embodiment, an apparatus is provided for detecting one or more of chemical and/or biological agents present in a sample. The apparatus comprises an emitter for positioning relative to a sample. The emitter is capable of emitting a terahertz signal directed at the sample. A detector is positioned relative to the sample to receive the interaction results of the emitted signal with the sample. Further, a processing element in communication with the detector is capable of processing the measured interaction results and performing a spectral analysis to determine the presence of one or more chemical and/or biological agents present in the sample.

Depending on the embodiment, the systems and methods may employ either laser or electronic means to generate terahertz signals and receive the interaction results. For example, laser methods use a laser to generate terahertz signals, and a phase-delayed or off-frequency laser to scan the interaction results from the sample. Electronic methods directly generate the terahertz signal and receive the interaction results. The measured interaction results are then processed to obtain the sample's spectral response across a band of terahertz frequencies.

In one embodiment, the detector is positioned to receive a resulting signal that propagates through the sample. This embodiment may employ a direct transmission terahertz spectrometer and a tube to direct the sample or sample flow between the emitter and detector. In an alternative or added embodiment, the detector is positioned to receive the interaction results signal that is reflected or back-scattered from the sample. This embodiment employs a reflective terahertz spectrometer. It may employ a tube to contain the sample, but it can also forgo the tube and observe the sample that is positioned, or flows across, the outside of the device, such as across the outside skin of a vehicle.

In one embodiment, the processing element performs a Fast Fourier Transform (FFT) of the resulting interaction results signal to obtain the sample's terahertz spectral response. One or more measured responses may be combined to form a resultant measured spectral response. Thereafter, it compares the measured spectral response to known responses to determine whether one or more chemical and/or biological agents are present in the sample, or to detect a composition change in a sample flow.

The systems and methods of the present invention may be implemented in a wide range of configurations and embodiments. As an example, the systems and methods may be employed on a vehicle to assess chemical and/or biological agents in the air. In this embodiment, the sample may be "captured in" or flowed through a chamber, such as a tube, for analysis; or it may examine the air or airflow occurring outside a stationary or moving vehicle. Where a tube is employed to contain the sample, a series of one or more filters may be employed to process the sample prior to testing. For example, an inlet design and tube design may utilize fluid dynamics to filter out wrong-sized particulates in the sample flow, to slow down the sample flow, or to compress or concentrate the sample prior to illumination with the terahertz emission.

Other aspects and features of the present invention, as defined solely by the claims, will become apparent to those ordinarily skilled in the art upon review of the following non-limited detailed description of the invention in conjunction with the accompanying figures.

DETAILED DESCRIPTION OF THE INVENTION

Figure 1:
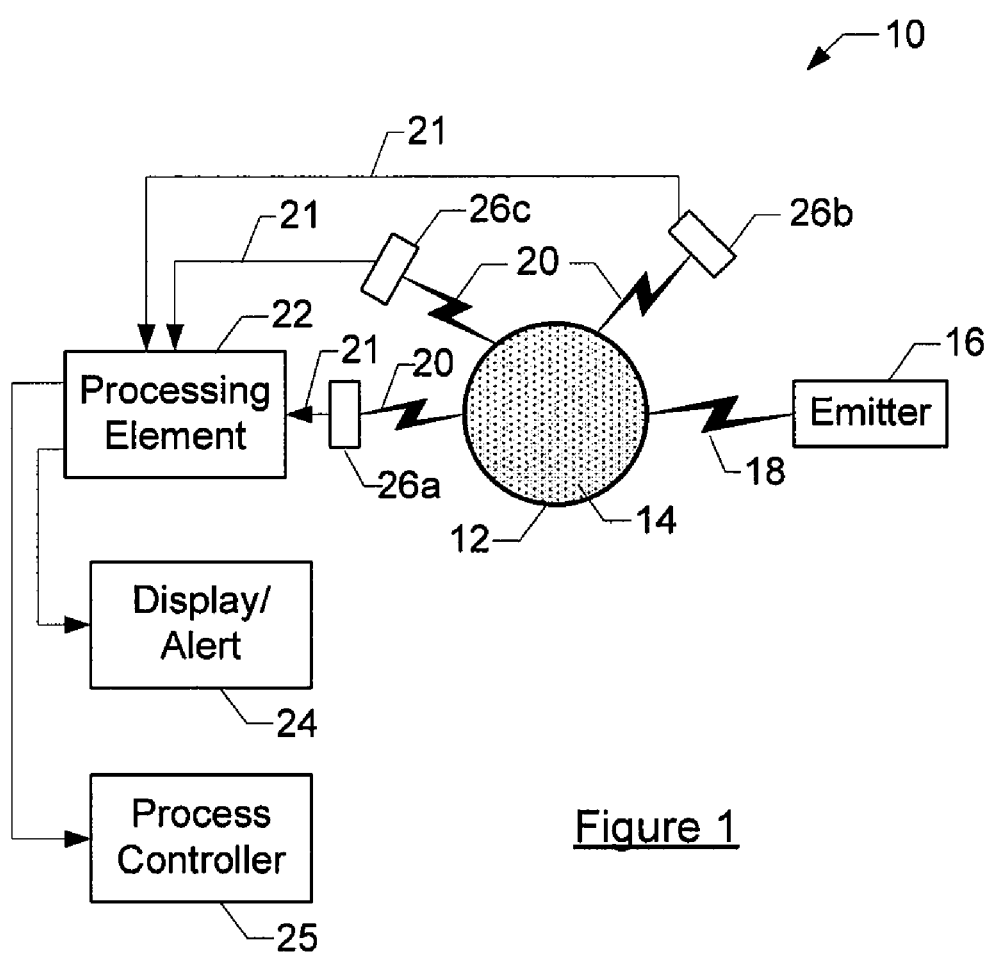
FIG. 1 is a block schematic diagram of a system for detecting one or more of a chemical and/or a biological agent present in a sample according to one embodiment of the present invention.

The following detailed description of embodiments refers to the accompanying drawings, which illustrate specific embodiments of the invention. Other embodiments having different structures and operations do not depart from the scope of the present invention.

As will be appreciated by one of skill in the art, the present invention may be embodied as a method, system, or computer program product. Accordingly, portions of the present invention may take the form of an entirely hardware embodiment, an entirely software embodiment (including firmware, resident software, micro-code, etc.) or an embodiment combining software and hardware aspects that may all generally be referred to herein as a "circuit," "module," "unit," or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a tangible medium such as a portable computer diskette, a hard disk, a random access memory (RAM), a read-only memory (ROM), an erasable programmable read-only memory (EPROM or Flash memory), an optical fiber, a portable compact disc read-only memory (CD-ROM), or other tangible optical or magnetic storage devices; or transmission media such as those supporting the Internet or an intranet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or other programming languages such as object code or assembly language. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The present invention provides systems and methods for detecting one or more of a chemical and/or a biological agent present in a sample, or to determine if the sample has deviated from "normal". The systems and methods use spectral analysis, rather than chemical reactions, to detect and assess chemical and/or biological agents. The systems and methods thus may eliminate the complex mechanisms needed for sample collection, concentration, isolation, and preparation to obtain a chemical reaction. Where a chemical-based solution is limited to a discrete number of analyses between replenishment of supplies; the systems and methods of the present invention may provide real time, continuous, semi real time, or substantially continuous analysis of a sample.

These advantages mean that the systems and methods of the present invention may be used for real-time evaluation. For example, when used in a vehicle, the systems and methods may be used to map a hazardous plume, or help guide a vehicle to either seek the plume or turn to avoid it. It can also be used as an alarm to declare that vehicle decontamination should be accomplished due to exposure to hazardous material; and it can help identify the contents of exposure. Its real-time capability immediately informs vehicle occupants that they should take appropriate actions due to exposure, enables immediate broadcast of warnings to others nearby, and its material ID can help guide choices in immediate medical treatment. By digitally recording its measurements of spectral signatures, it may provide a permanent record that can be used to substantiate exposures or enable further analysis post mission. Various sensors could be distributed in a network to provide area wide warnings and mapping capabilities.

The embodiments below discuss the systems and methods of the present invention in the context of a chemical/biological agent detector mounted in a vehicle such as an aircraft, car, etc. It is understood, however, that the systems and methods are not limited to this application, but instead may be used in any environment or system where chemical and/or biological testing is needed, or may be used to monitor sample flows to determine if the sample has deviated from "normal" and determine how to effect a change that will return the sample flow to "normal".

FIG. 1 illustrates a general embodiment of the invention. As illustrated, in this embodiment, the system 10 includes a sample chamber or tube 12 for "capturing" and/or otherwise housing a sample or sample flow 14 of a gas, liquid, or solid. For example, in one embodiment, the system could be used with a vehicle, where the tube 12 is placed in a location so as to collect air samples or water samples in the environment surrounding the vehicle. In another embodiment, the sample chamber 12 is not contained by a tube, but is the area immediately in the vicinity of the emitter 16.

Associated with the sample tube 12 is an emitter 16 for transmitting a terahertz signal 18 at the sample. One or more detectors 26 are provided to receive the resulting interaction results signal 20 after the terahertz signal has interacted with the sample 14. Further, a processing element 22 is connected to or in communication with the detectors 26 for analyzing the output signal 21 obtained from the detectors 26. The processor is connected to a display and/or an alert 24 to provide an indication if the sample includes one or more chemical and/or biological agents, or to a process controller 25 to cause a change that will affect the composition of the sample flow.

In one embodiment, the processing element may be a computer or computing element comprising a general processor. The processing element of this embodiment may further include a storage device comprising computer instructions for receiving and processing the resulting signal. For example, the storage may include various algorithms in the form of computer programming to implement known analysis procedures for identifying chemical and/or biological agents. It may also contain spectral response patterns for use in the analysis.

As illustrated in FIG. 1, depending on the type of set up, different detectors at different locations may be used. For example, detector/receiver 26a is positioned to receive a resulting signal propagated through the sample for analysis. Receiver 26b, on the other hand, is position to receive a reflected signal from the sample. Detector 26c may represent where multiple sensors are used at various locations to collect resulting signals from the sample.

In a general manner, a terahertz signal is directed at the sample 14. The sample absorbs or reflects a portion of the signal based upon its molecular structure. Through the use of terahertz spectroscopy, the absorption/reflection vs. frequency spectrum of the sample for a band of terahertz illumination frequencies can be generated. This measured spectral response of the sample is compared and analyzed using various techniques to previously measured spectral responses of known chemical and/or biological agents to determine the composition of the sample. When used with the process controller 25, the techniques could compare the measured response to previously measured responses of "normal" and "non-normal" sample flows to determine if a deviation has occurred, and how best to react to the deviation based upon its measured spectral response.

The spectral response is processed by the processing element 22. Analysis algorithms are used to discern the material makeup of the sample from the observations. In one embodiment, the spectral response for one time frame is analyzed. Another embodiment combines the spectral response across multiple time frames. These data are analyzed and compared to thresholds, sample patterns, or other methods to either discern the content of the sample or to discern a deviation from normal.

Spectral analysis provides several advantages over chemical reaction based testing. It allows continuous, real-time, non-destructive testing of the sample flow. Continuous testing always observes the sample. Real-time testing produces results without appreciable delay. Non-destructive testing does not consume, change, or destroy the sample. These characteristics make this system ideal for use in applications where real-time control based upon the sensed sample flow is needed to control a process or determine courses-of-action. In addition, spectral analysis does not require chemical or other resources (other than electricity) to perform the test. Thus, the system will generally not require the daily or periodic cleaning and maintenance that other systems require.

Figure 2:
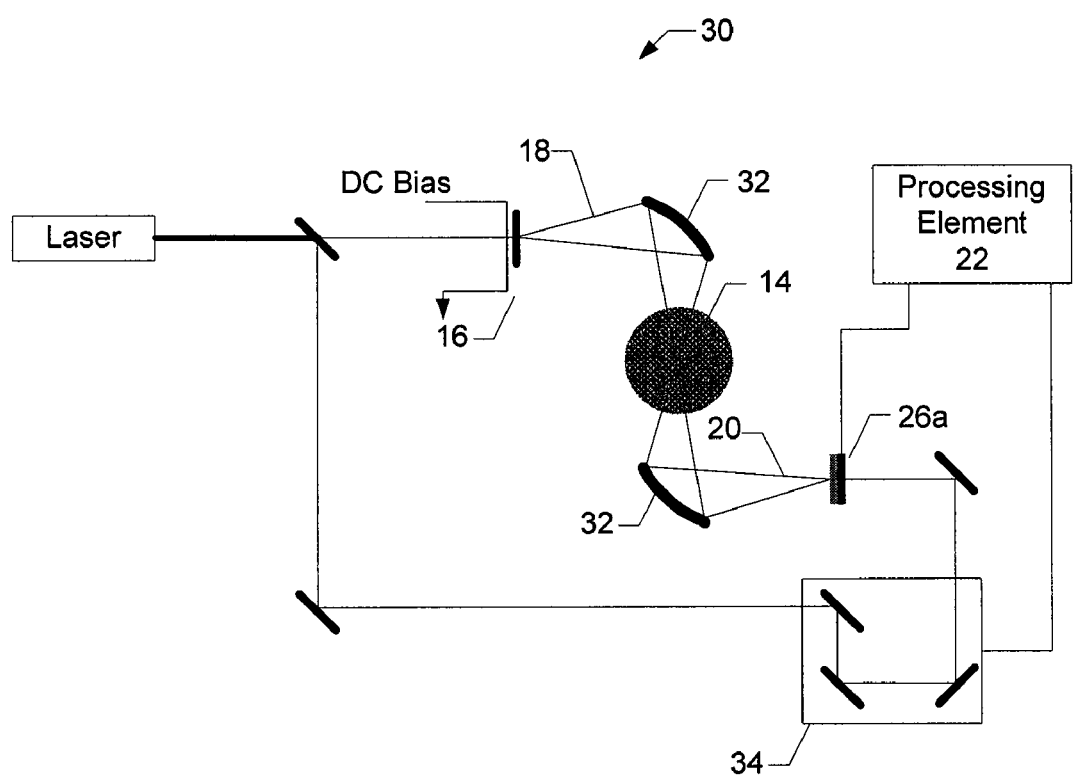
FIG. 2 is a block schematic diagram of a system for detecting one or more of a chemical and/or a biological agent present in a sample using transmission terahertz spectrometry according to one embodiment of the present invention.
Figure 3:
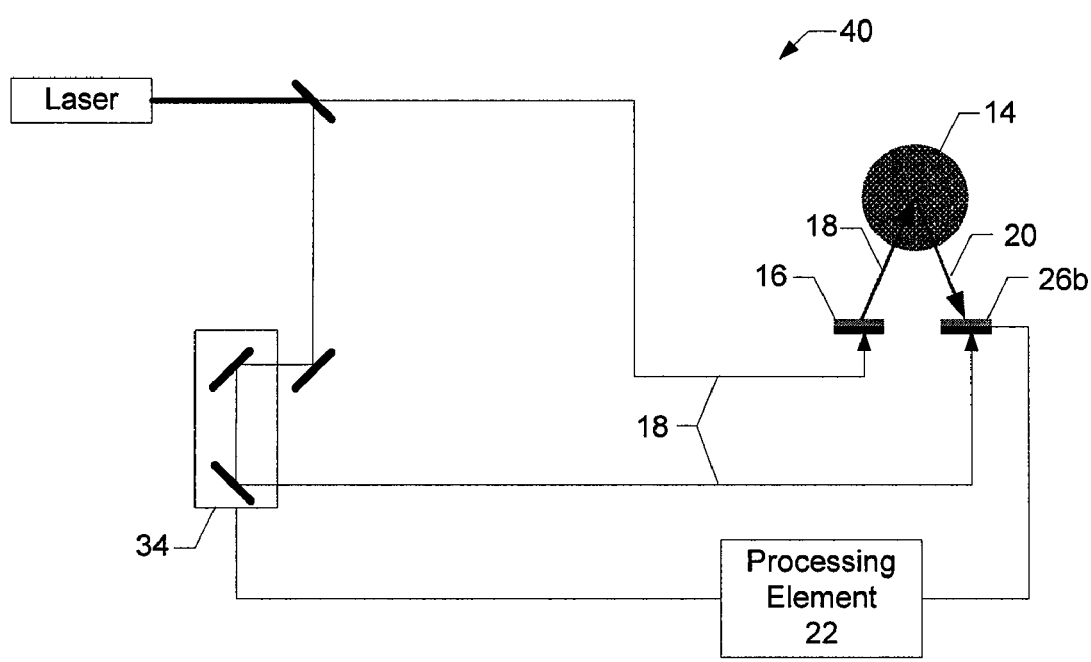
FIG. 3 is a block schematic diagram of a system for detecting one or more of a chemical and/or a biological agent present in a sample using reflective terahertz spectrometry according to another embodiment of the present invention.

FIGS. 2 and 3 illustrate alternative embodiments of the terahertz spectrometer portion of the system 10. Specifically, FIG. 2 illustrates a transmission system 30, wherein the generated signal 18 is transmitted through the sample. The sample is on a line between the emitter and the detector. Reflectors 32 are used to direct the emitted terahertz signal 18 toward the sample and the resulting signal 20 to detector 26a. As illustrated, the laser is also provided to the receiver 26a via an optical delay 34, where its terahertz effect combines with the resulting signal 20. The laser's optical delay is changed over time to produce a series of combined signals that can be Fourier Transformed to provide the spectral response. In this system the sample or sample flow is contained in a tube. This system measures terahertz absorption vs. frequency of the sample.

The reflective system 40 of FIG. 3 uses a detector 26b that is mounted next to the emitter. Both emitter and detector look in the same general direction, rather than at each other. The detector observes the sample's reflection of the emitter's terahertz signals, so it measures terahertz reflection vs. frequency of the sample. The sample for this system could be contained in a tube, but this system also has the advantage of being able to observe uncontained air flow, such as the air flow outside the skin of a vehicle.

Terahertz emitters and receivers are generally known in the art. The present invention envisions use of commercially available systems and methods for generation of terahertz test signals and capture of interaction results.

Depending on the embodiment, the systems and methods may employ either laser or electronic means to generate terahertz signals and receive the interaction results. For example, laser methods use a laser to generate terahertz signals, and a phase-delayed or off-frequency laser to scan the interaction results from the sample. Electronic methods directly generate the terahertz signal and receive the interaction results. The measured interaction results are then processed to obtain the sample's spectral response across a band of terahertz frequencies.

Based upon the results of the analysis, the systems and methods of the present invention have a wide variety of application. The systems and methods may be used in conjunction with a vehicle to analyze the environment surrounding the vehicle and provide alerts where chemical and/or biological agents are detected. This could be used to alert the occupants of danger, such that the occupants can take action to alter either their current route or location, seek decontamination of the vehicle, seek medical help, etc.

More specifically, in this embodiment, samples of the environment associated with the vehicle are captured and subjected to a test signal. The resulting spectral response signal is detected and analyzed for chemical and/or biological agents. Depending either on the type of agent and/or the level of the agent in the environment, the system generates alarms to the occupants and/or transmits alarms to remote locations to indicate potential danger, decontamination procedures should be employed, and/or medical help needed.

By continuing to take readings and provide alerts, the systems and methods could be used to "steer" the user of the vehicle to avoid the area where the chemical and/or biological agent is located. The system would provide information regarding changes in level of the detected chemical and/or biological agent over time.

Alternatively, the systems and methods could be used to "steer" the user of the vehicle toward the source or increased concentration of the chemical and/or biological agent, where the function of the vehicle to scout and pin point the source of the chemical and/or biological agent.

The systems and methods could also be used for early warning to other vehicles. For example, if two or more vehicles are traveling in an area and if the first vehicle detects a chemical and/or biological agent, it may alert the other vehicle to take evasive action. In this embodiment, the vehicle may include a transmitter capable of transmitting the alert to a remote location.

In some embodiments, the systems and methods could be used to map a geographic area. One or more vehicles may be deployed to take various sample readings over a given area and provide feedback regarding the presence of chemical or biological agents in a given area. In this embodiment, the vehicles navigation system is used to map the locations of various levels of the chemical and/or biological agent. When coupled with GPS readings, this information can provide an effective map of the expanse of the chemical and/or biological agent dispersion.

Additionally, the systems and methods could be used to monitor a manufacturing process to detect if and when the process deviated from normal. With appropriate design and calibration, the systems and methods could also identify what response should be executed to bring the process back to normal. In these embodiments, once a type and/or level of chemical and/or biological agent is detected feedback is provided to control the process.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," and "includes" and/or "including" when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. An apparatus for detecting one or more of a chemical and/or a biological agent present in a sample, said apparatus comprising:
   an emitter for positioning relative to a sample, wherein said emitter is capable of emitting a test signal having a terahertz wavelength directed at the sample;
   a detector for positioning relative to the sample to receive a resulting signal following interaction of the test signal with the sample; and
   a processing element in communication with said detector, wherein said processing element is capable of:
      determining a deviation of a spectral response of the resulting signal from a normal response; and
      comparing the deviation to a threshold, wherein the result of the comparison indicates the presence of one or more of a chemical and/or a biological agent present in the sample.

2. An apparatus according to claim 1, wherein the detector is positioned to receive a resulting signal that propagates through the sample.

3. An apparatus according to claim 1, wherein said apparatus comprises a sample tube for containing the sample, and wherein said emitter and detector are positioned to receive a resulting signal that propagates through the sample.

4. An apparatus according to claim 1, wherein the detector is positioned to receive a resulting signal that is reflected from the sample.

5. An apparatus according to claim 4, wherein the apparatus is located on a vehicle, wherein said emitter is positioned to emit a test signal into an environment associated with the vehicle, and said detector is positioned to receive a resulting signal reflected from the environment.

6. An apparatus according to claim 1, wherein said processing element is capable of performing a fast Fourier transform of the resulting signal and thereafter performing spectral analysis of the resulting signal to determine whether one or more chemical and/or biological agents is present in the sample.

7. An apparatus according to claim 1, wherein said processing element compares the spectrum of the resulting signal to known spectrums of either one or more chemical and/or biological agents to thereby determine chemical and/or biological agents in the sample.

8. An apparatus according to claim 1, wherein said apparatus further comprises a sample tube that employs an inlet design and tube design utilizing fluid dynamics to filter out wrong-sized particulates in the air, to slow down the sample, or to concentrate the sample prior to testing.

9. An apparatus according to claim 1, wherein the apparatus is located on a vehicle, and wherein said processing element issues an alert that the vehicle has been exposed to a chemical and/or biological agent.

10. An apparatus according to claim 9, further comprising a transmitter for transmitting the alert issued by said processing element to a remote location.

11. An apparatus according to claim 1, wherein the apparatus is located on a vehicle, and wherein said processing element issues an alert to a system controlling the vehicle for use in taking evasive action.

12. An apparatus according to claim 1, wherein the processing element is further capable of initiating an alert if the deviation is at least as great as the threshold.

13. An apparatus for monitoring a sample, said apparatus comprising:
an emitter for positioning relative to a sample, wherein said emitter is capable of emitting a test signal having a terahertz wavelength directed at the sample;
a detector for positioning relative to the sample to receive a resulting spectral response signal from the sample following interaction with the test signal;
a processing element in communication with said detector, wherein said processing element is capable of:
determining a deviation of a spectral response of the resulting signal from a normal response; and
comparing the deviation to a threshold.

14. An apparatus according to claim 13, wherein said processing element collects measurements from the sample over time and determines a deviation of the spectral response from a normal response.

15. An apparatus according to claim 13, wherein said processing element collects measurements from the sample from different locations within the sample and determines a deviation of the spectral response from a normal response.

16. An apparatus according to claim 13, wherein said processing element collects measurements from the sample over time and detects changes in a content of the sample over time.

17. An apparatus according to claim 16, wherein said processing element determines a cause for changes in the content of the sample.

18. An apparatus according to claim 13, wherein the sample is from a process, and said processing element issues an alert if the deviation is at least as great as the threshold, the alert being issued to a machine controlling the process to alter the process based on the alert.

19. An apparatus according to claim 13, wherein the processing element is further capable of initiating an alert if the deviation is at least as great as the threshold.

20. A method for detecting one or more of a chemical and/or a biological agent present in a sample, said method comprising:
emitting a test signal having a terahertz wavelength directed at the sample;
receiving a resulting signal following interaction of the test signal with the sample;
determining a deviation of a spectral response of the resulting signal from a normal response; and
comparing the deviation to a threshold, wherein the result of the comparison indicates the presence of one or more of a chemical and/or a biological agent present in the sample.

21. A method according to claim 20, wherein said receiving a resulting signal comprises receiving a resulting signal that propagates through the sample.

22. A method according to claim 20 further comprising capturing a sample in the sample tube, and wherein said receiving a resulting signal comprises receiving a resulting signal that propagates through the sample.

23. A method according to claim 20, wherein said receiving a resulting signal comprises receiving a resulting signal that is reflected from the sample.

24. A method according to claim 23, wherein the method is used with a vehicle, wherein said emitting a test signal emits a test signal into an environment associated with the vehicle, and said receiving a resulting signal comprises receiving a resulting signal reflected from the environment.

25. A method according to claim 20, wherein said performing a spectral analysis of the received signal comprises performing a fast Fourier transform of the resulting signal and thereafter performing spectral analysis of the resulting signal to determine whether one or more chemical and/or biological agents is present in the sample.

26. A method according to claim 20 further comprising comparing the spectrum of the resulting signal to known spectrums of either one or more chemical and/or biological agents to thereby determine chemical and/or biological agents in the sample.

27. A method according to claim 20, wherein the sample is from a gas or air flow, and wherein said method comprises filtering the sample to at least one of: filter out wrong-sized particulates, slow down air flow of the sample, or to concentrate the sample prior to testing.

28. A method according to claim 20 further comprising collecting measurements from the sample over time and said determining whether one or more chemical and/or biological agents is present in the sample comprises determining from the collected measurements the presence of one or more chemical and/or biological agents in the sample.

29. A method according to claim 20 further comprising collecting measurements from the sample from different locations within the sample and said determining whether one or more chemical and/or biological agents is present in the sample comprises determining from the collected measurements the presence of one or more chemical and/or biological agents in the sample.

30. A method according to claim 20 further comprising collecting measurements from the sample over time and said determining whether one or more chemical and/or biological agents is present in the sample comprises detecting changes in the content of one or more chemical and/or biological agents in the sample over time.

31. A method according to claim 30 further comprising determining a cause for changes in the content of one or more chemical and/or biological agents.

32. A method according to claim 20, wherein the sample is from a process, and said method further comprising issuing an alert if the deviation is at least as great as the threshold to a machine controlling the process to alter the process based on the alert.

33. A method according to claim 20, wherein the method is used with a vehicle, and said method further comprising issuing an alert, if the deviation is at least as great as the threshold, that the vehicle has been exposed to a chemical and/or biological agent.

34. A method according to claim 33, further comprising transmitting the alert to a remote location.

35. A method according to claim 20, wherein the method is used with a vehicle, and said method further comprising issuing an alert, if the deviation is at least as great as the threshold, to a system controlling the vehicle for use in taking evasive action.

36. A method according to claim 20, further comprising initiating an alert if the deviation is at least as great as the threshold.

37. An apparatus for detecting one or more of a chemical and/or a biological agent present in a sample, said apparatus comprising:

an emitter for positioning relative to a sample, wherein said emitter is capable of emitting a test signal having a terahertz wavelength directed at the sample;

a detector for positioning relative to the sample to receive a resulting signal following interaction of the test signal with the sample;

a processing element in communication with said detector, wherein said processing element is capable of processing the received signal and performing a spectral analysis to determine whether one or more chemical and/or biological agents is present in the sample; and a sample tube that employs an inlet design and tube design utilizing fluid dynamics to filter out wrong-sized particulates in the air, to slow down the sample, or to concentrate the sample prior to testing.

38. An apparatus for detecting one or more of a chemical and/or a biological agent present in a sample, said apparatus located on a vehicle, said apparatus comprising:

an emitter for positioning relative to a sample, wherein said emitter is capable of emitting a test signal having a terahertz wavelength directed at the sample;

a detector for positioning relative to the sample to receive a resulting signal following interaction of the test signal with the sample; and a processing element in communication with said detector, wherein said processing element is capable of:

processing the received signal and performing a spectral analysis to determine whether one or more chemical and/or biological agents is present in the sample; and issuing an alert to a system controlling the vehicle for use in taking evasive action.

* * * * *